United States Patent [19]

Sasaki et al.

[11] Patent Number: 5,466,572
[45] Date of Patent: Nov. 14, 1995

[54] HIGH SPEED FLOW CYTOMETRIC SEPARATION OF VIABLE CELLS

[75] Inventors: Dennis T. Sasaki, Mountain View, Calif.; Gerrit J. Van den Engh, Seattle, Wash.; Anne-Marie Buckie, Margate, United Kingdom

[73] Assignee: Systemix, Inc., Palo Alto, Calif.

[21] Appl. No.: 233,115

[22] Filed: Apr. 25, 1994

Related U.S. Application Data

[63] Continuation-in-part of Ser. No. 940,097, Sep. 3, 1992, abandoned.

[51] Int. Cl.[6] .................................................. A01N 1/02
[52] U.S. Cl. ................................. 435/2; 436/63; 436/172
[58] Field of Search .............................. 435/2, 7.1, 7.24, 435/240.1, 240.2; 436/63, 172

[56] References Cited

U.S. PATENT DOCUMENTS 5,061,620  10/1991  Tsikamoto .................. 435/7.21

OTHER PUBLICATIONS

Peters et al. Cytometry 6:290–301 (1985).
Van den Engh et al. Cytometry 10:282–293 (1989).
Visser in Flow Cytometry and Sorting 1990 Wiley–USS, Inc. pp. 669–683.
Reading et al. Blood 84:399a 1994.
Lidmo et al. in Flow Cytometry and Sorting 1990 Wiley–USS, Inc. pp. 145–169.
Peters in Flow Cytogenetics 1989 Academic Press pp. 211–224.
Gray et al. Science 238:323–329 (1987).
Tanke et al. Tibtech 11:54–62 (1993).

*Primary Examiner*—Margaret Parr
*Assistant Examiner*—Phillip Gambel
*Attorney, Agent, or Firm*—Bertram I. Rowland; Pamela J. Sherwood

[57] ABSTRACT

Hematopoietic cell populations are separated to provide cell sets and subsets as viable cells with high purity and high yields, based on the number of original cells present in the mixture. High-speed flow cytometry is employed using light characteristics of the cells to separate the cells, where high flow speeds are used to reduce the sorting time.

8 Claims, No Drawings

HIGH SPEED FLOW CYTOMETRIC SEPARATION OF VIABLE CELLS

REFERENCE TO GOVERNMENT RIGHTS

The work disclosed herein was supported by a contract between the Regents of the University of California and the United States Department of Energy for the operation of the Lawrence Livermore National Laboratory, contract number W-7405-ENG-48. The United States Government may have certain rights in this invention.

CROSS-REFERENCE TO RELATED APPLICATIONS

This application is a continuation-in-part of application Ser. No. 07/940,097, filed Sep. 3, 1992, now abandoned.

INTRODUCTION

1. Technical Field

The field of this invention is the high speed flow cytometric separation of cell subsets.

2. Background

There is an extraordinary variety of cells in animals. Cells which make up various organs and tissues may include a great variety of different types of cells having different functions and interacting to form different structures. In many situations, the isolation of the tissue or organ results in a complex mixture of cells, where one set or subset of cells may be desired. This is graphically exemplified by hematopoietic cells, particularly as found in bone marrow and the peripheral blood, as well as many lymphoid organs.

One of the most versatile ways to separate cells is by use of flow cytometry, where the particles, i.e. cells, can be detected by fluorescence or light scattering. However, due to the low processing rate common to commercially-available cell sorters, purification of a small population from large quantities of cells is not feasible.

Exemplary of the situation with cells is the attempt to purify large numbers of chromosomes for the production of recombinant DNA libraries or gene mapping. Calculations indicate that a commercial cell sorter processing at an average 2000 events per second would require over 120 hours in order to obtain 1 μg of DNA (Cremer, et al., Human Genet. 60, 262–266 [1982]).

A high speed sorter has been recently developed at the Lawrence Livermore National Laboratory which is able to routinely purify large quantities of human chromosomes in a few hours, where commercially-available cell sorters would take several days. This sorter is described in Gray, et al., *Science* 238, 323–329 (1987); Peters, (1989), *Chromosome purification by high-speed sorting*. Gray, J. (ed), In "Flow Cytogenetics." London; Academic Press, pp. 211–224; Peters, et al., *Cytometry* (1985)6, 290–301; van den Engh and Stokdijk, *Cytometry* (1989) 10, 282–293).

While the sorter has been successful with chromosomes, the manner in which it achieves the high speed would be expected to put extraordinary stresses on viable cells. A technological difference in the available commercial systems and a high speed sorter lies in the significantly increased generation of stable droplets. Augmented droplet formation, combined with the occupance of particles following Poisson statistics, ensures that an increased amount of "space" exists between the events to diminish the likelihood of rejection due to coincidence. This factor alone minimizes the probability of having more than one event per droplet. Design considerations which are incorporated into a high-speed sorter to obtain greater droplet frequencies include greater operational pressure handling (30–100 psi) as compared to conventional sorters which use about 10 psi, in order to force liquid through the nozzle at a higher rate, an acoustic oscillator with ultrasonic frequency capabilities (up to 200 KHz as compared to 20–30 KHz in a commercial sorter), droplet charging and deflection electronic subsystems, and high-speed digital processing electronics. For descriptions of each of these components, see the Experimental section.

It is therefore of substantial interest to determine whether parameters can be defined where viable cells can be efficiently sorted at high speeds, so as to give high yields of cell subset populations, with substantial retention of viability, retention of phenotype, and high efficiency in the proportion of cells isolated which are available, as well as the purity of the population obtained.

SUMMARY OF THE INVENTION

Cells are isolated from a mixture, where the desired population is a small fraction of the total cellular population. The subset of interest is isolated by differential fluorescent marking between the subset of interest and the other cells present and sorting through a high-speed cell sorter. The subset can be obtained as viable cells in high purity with high efficiency as compared to the number of cells originally present in the population.

DESCRIPTION OF THE SPECIFIC EMBODIMENTS

Viable cells are separated into two or more different populations at high speed and high efficiency to provide subsets of viable cells of high purity. The cell types can be widely varied, including hematopoietic cells, neuronal cells, endothelial cells, epithelial cells, fibroblasts, myoblasts, mesenchymal cells, natural killer (NK) cells, maternal/fetal erythroid cells, and the like. The cells of particular interest are hematopoietic cells, which include progenitor and mature cells of the lymphoid, myelomonocytic and erythroid lineages, as well as stem cells (the original progenitors) and subsets of these cells, such as T-cells and subsets of T-cells, such as CD4+ and CD8+. Cells having specific surface membrane proteins, such as T-cells having a specific variable region, specific homing receptors, growth factor, hormone and colony stimulating factor (CSF) receptors, neurotransmitter receptors, or the like are also of interest. The cells may be derived from any animal, particularly mammalian or avian species, including primate, particularly human, murine, particularly mouse, equine, bovine, ovine, porcine, lagomorpha, canine, feline, etc.

The source of the cells may be any source which is convenient. Thus, various tissues, organs, fluids, or the like may be the source of the cellular mixtures. Of particular interest are bone marrow and peripheral blood, although other lymphoid tissues are also of interest, such as spleen, thymus, and lymph node. For use in flow cytometry, cells from solid tissue will normally be dispersed in an appropriate medium.

The cellular compositions that are introduced into the high-speed flow cytometer may or may not have been subjected to prior treatment. Prior treatments may involve removal of cells by various techniques, including centrifugation, using Ficoll-Hypaque, panning, affinity separation, using antibodies specific for one or more markers present as surface membrane proteins on the surface of cells, or other technique, which provides enrichment of the set or subset of cells of interest. Usually, the cellular composition of hematopoietic cells separated by high-speed flow cytometry will have not more than about 5 no. %, usually not more than about 2 no. %, and more usually not more than about 1 no. % of the cells of interest, and will usually have at least about 0.01 no. %, preferably at least about 0.02 no. %, and preferably at least about 0.05 no. % of the cells of interest. See, for example, U.S. Pat. No. 5,061,620.

Cells of interest will usually be differentiated by virtue of surface membrane proteins which are characteristic of the cells. For example, CD34 is a marker for immature hematopoietic cells. Markers for dedicated cells include CD 10, CD19, CD20, and sIg for B cells, CD 15 for granulocytes, CD 16 and CD33 for myeloid cells, CD 14 for monocytes, CD41 for megakaryocytes, CD38 for lineage dedicated cells, CD3, CD4, CD7, CD8 and T cell receptor (TCR) for T cells, Thy-1 for progenitor cells, glycophorin for erythroid progenitors and CD71 for activated T cells. In isolating early progenitors, one may divide a CD34 positive enriched fraction into lineage (Lin) negative, e.g. CD2–, CD 14–, CD15–, CD16–, CD10–, CD19–, CD33– and glycophorin A–, fractions by negatively selecting for markers expressed on lineage committed cells, Thy-1 positive fractions, or into CD38 negative fractions to provide a composition substantially enriched for early progenitor cells. Other markers of interest include $V\alpha$ and $V\beta$ chains of the T-cell receptor.

The medium in which the cells are sorted will be any medium which maintains the viability of the cells. A preferred medium is phosphate buffered saline containing from 0.1 to 0.5 % fetal calf serum. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, etc., frequently supplemented with fetal calf serum.

The basis for separation in the high-speed flow cytometer will depend upon the light detectable characteristics of the cells. Thus, various light characteristics can be used in the cell sorter, which characteristics include light scatter and fluorescence, where the flow cytometer can detect the effect of a cell on a laser light beam. Depending upon the nature of the cell composition, various characteristics can be employed.

As markers, a wide variety of fluorescent molecules can be employed, which may be conjugated as labels to antibodies specific for cellular markers which identify particular sets and subsets of cells. Ligands to receptors may be conjugated, where the ligands may be naturally occurring or synthetic, proteins, saccharides, synthetic organic molecules or the like, or molecules which bind to other molecules, such as major histocompatibility complex-T cell receptor (MHC-TCR) combinations, etc. Fluorescent markers which are available include fluorescein, Texas Red, phycobiliproteins, allophycocyanin, cyanine derivatives, rhodamine, and tandem conjugates for surface markers and a host of fluorescent probes used to indicate physiological development and nuclear parameters.

The cell suspension is brought to the nozzle assembly under positive pressure, and introduced to the center of the sheath flow. The physical properties of fluid laminar flow then "focuses" the incoming cell suspension into a single file which is confined in the center of the fluid jet. The fluidic settings which control the conditions of operation for the high-speed flow cytometer are interrelated. The nozzle diameter, system pressure and droplet frequency are independently set. The jet velocity is related to the system pressure and nozzle diameter as described below. The droplet delay is set after empirical calibration with a standard sample.

The system pressure for the fluidics will generally be set for at least about 20 psi and not more than about 80 psi, usually not more than about 75 psi. Preferably, the system pressure will be in the range of about 30–60 psi, more preferably about 40 psi. The nozzle diameter will be at least about 25 μm, more usually at least about 30 μm and not more than about 100 μm, preferably about 40–80 μm, more preferably about 70 μm. The droplet frequency will be at least about 40 KHz, usually not more than about 150 KHz. Preferably the frequency will be in the range of about 50–90 KHz, more preferably about 60 KHz.

System pressure and calculated velocity for the stream are related. Experimentally, the relationship has been shown to have a rectangular curve, in which a plateau is reached for jet velocity, and increased pressure has a minimal effect. At the operating conditions for system pressure used in viable cell sorting, the jet velocity generally will be at least about 15 m/s, more usually at least about 20 m/s and not more than about 30 m/s, generally ranging from about 20–25 m/s.

Within the design of the sort electronics is a feature that determines the point in time in which a droplet containing a cell (or calibration particle) arrives at the point where it can be pulled out of the main trajectory and sorted for its designated criteria. The starting point begins at the interception point of the laser beam and the cell of interest. One then determines the distance or time required for the identified cell to get to the drop formation point. The exact time or distance is then applied from the drop breakoff point to the point of deflection segment. The setting for the delay time is slightly variable from run to run and with a given operating pressure and oscillator frequency and amplitude, and will range from 100 μs to 200 μs, more usually from 150 μs to 180 μs at 40 psi. The optimal setting is determined by a calibration run with particles of defined size and fluorescence. The procedure for testing this calculation is by varying the number of droplet cycles around the calculated mean cycle and sorting a set number of calibration particles onto a slide. The sorted droplets for each drop cycle are then examined under a fluorescence microscope and a frequency chart established. The optimal drop point is the setting where the expected number of particles has been deposited. Normally, the distribution of particles about the optimum delay setting follows a normal, Gaussian distribution. As an example, in one run with the operational pressure of 40 psi and a drop drive frequency of 62 Khz, it was found that the optimal breakoff point had a mean of 174 μs.

The droplet occupancy will usually be at least 1%, more usually at least 5% and not more than about 25%, frequently not more than about 20%, generally in the range of about 15–20%.

The resulting sample flow rate will generally be at least about 10,000 events per second, more usually at least about 12,000 events per second, and generally not more than about 35,000 events per second, more usually not more than about 25,000 events per second, preferably in the range of about 15,000–20,000 events per second. The fluidic settings at which such a sorting speed can be achieved will vary from machine to machine since the quality and condition of valves, nozzles and oscillators will vary.

The cells may be collected in any appropriate medium which maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum. The cells may then be used as appropriate. In some instances, it may be desirable to remove any antibody markers, where the cells may be flooded with molecules which are competitive for the monoclonal antibodies with the surface membrane proteins, so as to substantially remove the antibodies from the surface. The cells may then be washed free of the competitor and the antibodies which are non-specifically bound and may then be used.

The cells find a wide variety of applications. Where hematopoietic stem cells are involved, these may be used for bone marrow transplantation, for identification of growth factors, and for production of various hematopoietic cell progenitor cell subsets by employing appropriate growth factors. For specific T-cells, these cells may find use in the treatment of cancer as in the case of tumor-infiltrating lymphocytes, for identification of T-cells associated with specific diseases, e.g. autoimmune diseases, for B-cells having particular sIg binding to a specific epitope of interest, and the like.

The following examples are offered by way of illustration and not by way limitation.

EXPERIMENTAL

EXAMPLE I.

Sorting Murine Hematopoietic Cells

Murine bone marrow was obtained from BA1.1 mice and processed to remove red cells and granulocytes by density gradient (Nycodenz™). Cells were then resuspended in cold Hank's Basic Salt Solution ("HBSS") containing propidium iodide to discriminate viable cells (Sasaki, et al., *Cytometry* (1987) 8,413).

A high-speed flow cytometry sorter was employed (Gray, et al. *Science* (1987) 238, 323–329; Peters (1989), *Chromosome purification by high-Speed sorting*. Gray, J. (ed), In "Flow Cytogenetics." London; Academic Press, pp. 211–224; Peters, et al., *Cytometry* (1985) 6, 290–301; van den Engh and Stokdijk, *Cytometry* (1989) 10, 282–293). Visible laser excitation (488 nm) was employed. Latex calibration particles were run to check the position of scatter and fluorescence detectors. The system pressure for the fluidics was set at 60 psi with a jet emanating from a 50 μm diameter nozzle at a calculated velocity of 23 m/s. The droplet frequency was set at 100 KHz. These particles were also used to the determine the optimal droplet delay setting.

When the system was performing according to the calibration factors, the mouse bone marrow sample was placed on the instrument. The detectors were then adjusted to resolve the scatter profile of the lymphoid from myeloid cells. The sample flow rate was then adjusted to 17,000 events per second. Resolution of the scatter profile changed slightly, compared to previous visualizations on the FACStar due to the elasticity of the cells in the high-pressure/high velocity system. Neutrophils were found to remain intact going through the system and were clearly resolvable.

Five separate runs were performed on the same sample. One run was performed at a throughput at 13,000 events per second followed by three at 17,000 per second and one at 18,000 events per second. Four of the runs were based on the gating of all leucocytes from RBC and debris in the scatter profile and one gated on the lymphoid cells. Drop delay times were also varied. $10^6$ gated cells were collected in each of the runs in under 5 min. Sorted cells were collected in plastic tubes containing fresh medium and immediately placed on ice for storage.

TABLE 1

Sort variables

| | | | |
|---|---|---|---|
| Sort 1: | 18,000 per second | Delay = 103 | Gated on WBC scatter |
| Sort 2: | 17,000 per second | Delay = 103 | Gated on WBC scatter |
| Sort 3: | 17,000 per second | Delay = 100 | Gated on WBC scatter |
| Sort 4: | 13,000 per second | Delay = 106 | Gated on WBC scatter |
| Sort 5: | 17,000 per second | Delay = 103 | Gated on lymphoid scatter |

Portions ($5 \times 10^5$ cells) of the sorted samples were analyzed on a Becton-Dickinson FACScan flow cytometer. Purity for all samples based on scatter profiles was better than 85% based on corresponding gate criteria. Cell counts and viability using Trypan blue showed viability greater than 90%.

$5 \times 10^5$ cells of each of the sorted samples were used for injections into C57BL/6 mice. $1 \times 10^5$ cells were used in 4 mice for sort 1–3 by injecting the cell suspension in the sub-orbital sinus of the animals. Three mice were injected using sort faction 4. Only $3 \times 10^4$ cells were injected into 3 mice from the sort 5 fraction, gated on lymphoid. The presence of spleen colonies from the injected mice were ascertained from these animals after 13 days (Spangrude, et al. (1988) *Science* 241:58–62). Control mice formed no spleen colonies.

TABLE 2

Spleen colony results.

| Sorted Fraction | Spleen Colonies |
|---|---|
| 1. | 10, 5, 9, 10 |
| 2. | 10, 9, 8, 9 |
| 3. | 10, 11, 8, 9 |
| 4. | x, 7, 9 |
| 5. | 1, 3, 2 |

EXAMPLE II

Sorting Human Hematopoietic Cells

Peripheral blood lymphocytes were obtained from random normal donors from the Stanford University Blood Bank and stored in liquid nitrogen. For use, they were thawed rapidly and counted for cell number and viability. The starting population of the thawed cells revealed 80% viability. The cells were then run as a sample on the high speed cell sorter at various operational pressures to determine whether the increased velocity and decompression on the cells would cause a significant loss of viability. Cells were collected from each trial into a tissue culture tray well, and then counted for cell viability by Trypan blue exclusion.

The sorting of cells was performed on a modified, dual-laser, modular flow cytometer system. Based upon stable fluid function calculations from the principles described by Rayleigh, we ran the system at an operational pressure of 44 psi to generate a fluid jet velocity of 20 m/s (4.5 ml/min) from a 70 micron BDIS ceramic nozzle. A drop drive frequency of 60.5 KHz using a Fluke Model PM5/38 10 MHz function generator was used, and a laser intercept to drop break off distance of 11 mm. All samples were sorted at rates of 10,000 to 40,000 cells per second using a single drop deflection scheme. The useable sort rate was determined as a sunction of cell concentration and minimization of abort frequencies greater than 10%.

Results:

| System Pressure | % Cells Viable |
| --- | --- |
| 10 psi | 81% |
| 20 psi | 83% |
| 30 psi | 84% |
| 40 psi | 73% |

-continued

Results:

| System Pressure | % Cells Viable |
| --- | --- |
| 50 psi | 79% |
| 60 psi | 81% |

The data shows that there is no deleterious effects, within the range used, of increased operational pressure on fragile, thawed, human lymphocytes.

Sorting experiments were performed on peripheral blood cells from patients, using a cocktail of antibodies which define lineage ($CD34^-lin^+$), progenitor ($CD34^+lin^-$) and stem cell ($CD34^+thy-1^+lin^-$) compartments. Antibody stained cells were brought to the sorter at cell concentrations of $5-10\times10^6$ cells/ml in $Ca^+Mg^+$–free Dulbecco's phosphate buffered saline containing 0.5% serum. The sort gates were then established using isotype matched controls as well as positive, single color control samples. A portion of the patient samples were also sorted on a Becton-Dickinson FACS Vantage as an instrument control as a way of comparing speed, cell detection and purity factors.

Frozen cells from Patient 1 mobilized peripheral blood were thawed, then stained with anti-CD34 Texas Red, anti-CD 14 and CD 15 FITC, and anti-Thy-1 PE. The initial cell viability was determined to be 42% by Trypan blue exclusion. Cells were gated for the stem cell phenotype of $CD34^+$ $thy-1^+$ lin–. The cells were then run as a sort sample at two throughput rates. The collected cells were assayed for viability, and placed in methylcellulose for CFU determination at a concentration of 5,000 cells per well.

Patient 2 cells from day 5 mobilized peripheral blood of a multiple myeloma patient were prepared from buffy coat, then hypotonically lysed with ammonium chloride to eliminate erythrocytes. Cells were stained and gated as for patient 1. Cells were sorted at 5,000; 25,000 and 35,000 events per second. 200,000 cells were collected for each condition, and the viability determined. Six hundred cells were then placed into each well of methylcellulose cultures.

Patient 3 cells were elutriated cells from the peripheral blood of a breast cancer patient. Erythrocytes were hypotonically lysed using ammonium chloride, and stained and sorted as described. Six hundred cells per well were plated in methylcellulose cultures.

Methylcellulose cultures contained SCF (stem cell factor) IL-3, GM-CSF and erythropoietin. The presence or formation of specific morphological colonies (BFU-E, CFU-GM and CFU-mix) were scored by eye after two weeks in vitro, indicating the presence of functional progenitor cells.

Results:

|  | % Viable | Sort Rate | CFU-GM | BFU-E | CFU-mix |
| --- | --- | --- | --- | --- | --- |
| Patient 1 | 98.7% | 5,000 | 187 ± 19 | 60 ± 71 | 173 ± 47 |
|  | 96.3% | 13,000 | 207 ± 9 | 53 ± 25 | 147 ± 34 |
| Control | >95% | 5,000 | 67 ± 68 | 73 ± 77 | 100 ± 71 |
| Patient 2 | 99% | 5,000 | 287 ± 79 | 56 ± 79 | 56 ± 79 |
|  | 99% | 25,000 | 167 ± 136 | 167 ± 136 | 111 ± 79 |
|  | 99% | 35,000 | 167 ± 0 | 278 ± 208 | 724 ± 284 |
| Control | >95% | 3,000 | 0 | 0 | 56 ± 79 |
| Patient 3 | >95% | 3,000 | 501 ± 0 | 2,255 ± 450 | 2,129 ± 380 |
|  | >95% | 25,000 | 1,127 ± 432 | 2,923 ± 608 | 6,638 ± 991 |

The data shows that functional, viable human hematopoietic cells can be obtained after high speed sorting.

It is evident from the above results, that the subject process allows for the efficient separation of small numbers of cells in a highly mixed large population of cells. High purity and efficiency of separation can be achieved, where the cells retain viability and their ability to proliferate, as demonstrated by the formation of spleen colonies and in vitro assays. Thus, the subject method provides the ability to separate a small proportion of cells from a large number of cells for use in a large variety of applications.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. In a method for separating a viable hematopoietic cell population subset from a mixture of cells using flow cytometry, wherein the improvement comprises:

contacting said mixture of cells with a fluorescent labeled molecule which specifically binds a surface membrane protein of said subset; and passing a stream of said cells through a nozzle having a diameter of from about 25 to 100 μm at a pressure in the range of about 30–100 psi to provide a jet velocity in the range of about 15 to 30 m/s and a droplet frequency in the range of about 50 to 100 KHz, wherein the resulting sample flow rate will be in the range of about 10,000 to 35,000 events per second; and isolating a viable cell population subset.

2. A method according to claim 1, wherein said subset is stem cells.

3. A method according to claim 2, wherein said stem cells are human.

4. A method according to claim 3, wherein said fluorescent labeled molecule is a monoclonal antibody which specifically binds human Thy-1.

5. A method according to claim 3, wherein said mixture of cells is enriched for CD34-positive cells.

6. A method according to claim 3, wherein said mixture of cells is depleted for CD38-positive cells.

7. A method according to claim 1, wherein said stream comprises a nutrient medium.

8. A method according to claim 1, wherein said subset comprises fewer than about 1% of the cells of said mixture and the purity of said separated subset is greater than about 80%.

* * * * *